(12) United States Patent
Meng et al.

(10) Patent No.: US 8,585,630 B2
(45) Date of Patent: Nov. 19, 2013

(54) IMPLANTABLE INTRAOCULAR PRESSURE DRAIN

(75) Inventors: Ellis Fan-chuin Meng, Pasadena, CA (US); Po-Jui Chen, Pasadena, CA (US); Damien Rodger, Los Angeles, CA (US); Yu-Chong Tai, Pasadena, CA (US); Mark Humayun, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/555,329

(22) Filed: Jul. 23, 2012

(65) Prior Publication Data

US 2012/0289883 A1   Nov. 15, 2012

Related U.S. Application Data

(62) Division of application No. 11/205,757, filed on Aug. 16, 2005, now Pat. No. 8,246,569.

(60) Provisional application No. 60/602,110, filed on Aug. 17, 2004.

(51) Int. Cl.
    *A61M 5/00* (2006.01)
(52) U.S. Cl.
    USPC .................................................. 604/8; 604/9
(58) Field of Classification Search
    USPC ............. 604/8–10, 106, 107, 246, 264, 289, 604/290, 294, 523
    See application file for complete search history.

(56) References Cited

U.S. PATENT DOCUMENTS

| | | | | |
|---|---|---|---|---|
| 3,788,327 | A | * | 1/1974 | Donowitz et al. ............. 604/247 |
| 4,402,681 | A | | 9/1983 | Haas et al. |
| 4,604,087 | A | | 8/1986 | Joseph |
| 5,073,163 | A | | 12/1991 | Lippman |
| 5,338,291 | A | | 8/1994 | Speckman et al. |
| 5,370,607 | A | | 12/1994 | Memmen |
| 5,626,558 | A | * | 5/1997 | Suson ............................... 604/8 |
| 5,629,008 | A | * | 5/1997 | Lee ............................... 424/426 |
| 5,830,173 | A | | 11/1998 | Avery et al. |
| 6,029,672 | A | | 2/2000 | Vanney et al. |

(Continued)

OTHER PUBLICATIONS

Chen et al. "Spiral-tube parylene intraocular pressure sensor," Proceedings, The 18th IEEE International Conference on Micro Electro Mechanical Systems (MEMS '05), Miami Beach, Florida, USA, pp. 311-314, Jan. 2005.

(Continued)

*Primary Examiner* — Philip R Wiest
(74) *Attorney, Agent, or Firm* — Bingham McCutchen LLP

(57) ABSTRACT

An implanted parylene tube shunt relieves intra-ocular pressure. The device is implanted with an open end in the anterior chamber of the eye, allowing excess fluid to be drained through the tube out of the eye. In one embodiment, only a first end of the tube implanted into the anterior chamber of the eye is open. Intra-ocular pressure (IOP) is then monitored, for example utilizing an implanted sensor. When IOP exceeds a critical valve, a practitioner intervenes, puncturing with a laser a thinned region of the tube lying outside the eye, thereby initiating drainage of fluid and relieving pressure. In accordance with alternative embodiments, the both ends of the tube are open, and the tube includes a one-way valve configured to permit drainage where IOP exceeds the critical value. The tube may include projecting barbs to anchor the tube in the eye without the need for sutures.

6 Claims, 20 Drawing Sheets

(56) References Cited

U.S. PATENT DOCUMENTS

| | | | |
|---|---|---|---|
| 6,203,513 | B1 | 3/2001 | Yaron et al. |
| 6,280,449 | B1 | 8/2001 | Blake |
| 6,294,263 | B1 | 9/2001 | Okudaira et al. |
| 6,440,164 | B1 | 8/2002 | DiMatteo et al. |
| 6,471,666 | B1 * | 10/2002 | Odrich .................. 604/8 |
| 6,508,779 | B1 * | 1/2003 | Suson .................. 604/8 |
| 6,558,315 | B1 | 5/2003 | Kuyava |
| 6,605,093 | B1 | 8/2003 | Blake |
| 6,699,394 | B2 | 3/2004 | Tai et al. |
| 6,881,198 | B2 | 4/2005 | Brown |
| 7,144,616 | B1 | 12/2006 | Unger et al. |
| 2002/0109114 | A1 | 8/2002 | Driggs et al. |
| 2003/0028076 | A1 | 2/2003 | Kuyava et al. |
| 2003/0120200 | A1 | 6/2003 | Bergheim et al. |
| 2003/0135149 | A1 | 7/2003 | Cullen et al. |
| 2004/0039401 | A1 | 2/2004 | Chow et al. |
| 2004/0073156 | A1 | 4/2004 | Brown |
| 2004/0220510 | A1 | 11/2004 | Koullick et al. |
| 2006/0018360 | A1 | 1/2006 | Tai et al. |
| 2007/0112263 | A1 | 5/2007 | Fink et al. |

OTHER PUBLICATIONS

Clark et al., "Deformations and Stresses in Bourdon Tubes" Journal of Applied Physics—Dec. 1950—vol. 21, Issue 12, pp. 1340-1341.

Ethier et al., "Ocular biomechanics and biotransport," Annu Rev Viomed Eng, vol. 6, pp. 249-273 (2004).

He et al., "Parylene Neuro-cages for Live Neural Networks Study," Technical Digest, The 12th IEEE International Conference on Micro Electro Mechanical Systems (MEMS '03), Kyoto, Japan, Jan. 19-23, pp. 602-605, 2003.

Liger et al., "Robust Parylene-to-Silicon Meachanical Anchoring," Proceedings, The Sixteenth IEEE International Conference on Micro Electro Mechanical Systems (MEMS '03), Kyoto, Japan, Jan. 19-23, pp. 602-605, 2003.

Meng, "High aspect ratio parylene etching for microfluidics and bioMEMS," Proceedings, 2004 Micro Total Analysis System (uTAS '04), Malmo, Sweden, Sep. 26-30, pp. 401-403, 2004.

Meng et al., "Polymer MEMS for Micro Fluid Delivery Systems," in Polymer Preprints, vol. 44., New York, New York, pp. 552-553 (2003).

Meng, "A check-Valved Silicon Diaphram Pump," MEMS 2000, Miyazaki, Japan, Jan. 2000.

Molteno, "New implant for drainage in glaucoma: clinical trial" Br J Opthalmol 53 (1969), pp. 606-615.

Schwartz et al., "Current management of glaucoma," Curr Opin Ophthalmol, vol. 15, pp. 119-126 (2004).

Wang et al., "A Normally Closed in-Channel Micro Check Valve," in MEMS 2000 Miyazaki, Japan, (2000).

"What is Parylene?" downloaded from the Internet at http://www.conformal-coating.com/parylene_coating.htm at Sep. 25, 2006.

Xie et al., "Integrated Surface-Micromachined Mass Flow Controller," Proceedings, The Sixteenth IEEE International Conference on Micro Electro Mechanical Systems (MEMS '03), Kyoto, Japan, Jan. 19-23, pp. 20-23, 2003).

Xie et al., "Integrated electrospray chip for mass spectrometry," Proceedings, Micro Total Analysis Systems 2002 (TAS '02), Nara, Japan Nov. 3-7, 2002, pp. 709-711.

* cited by examiner

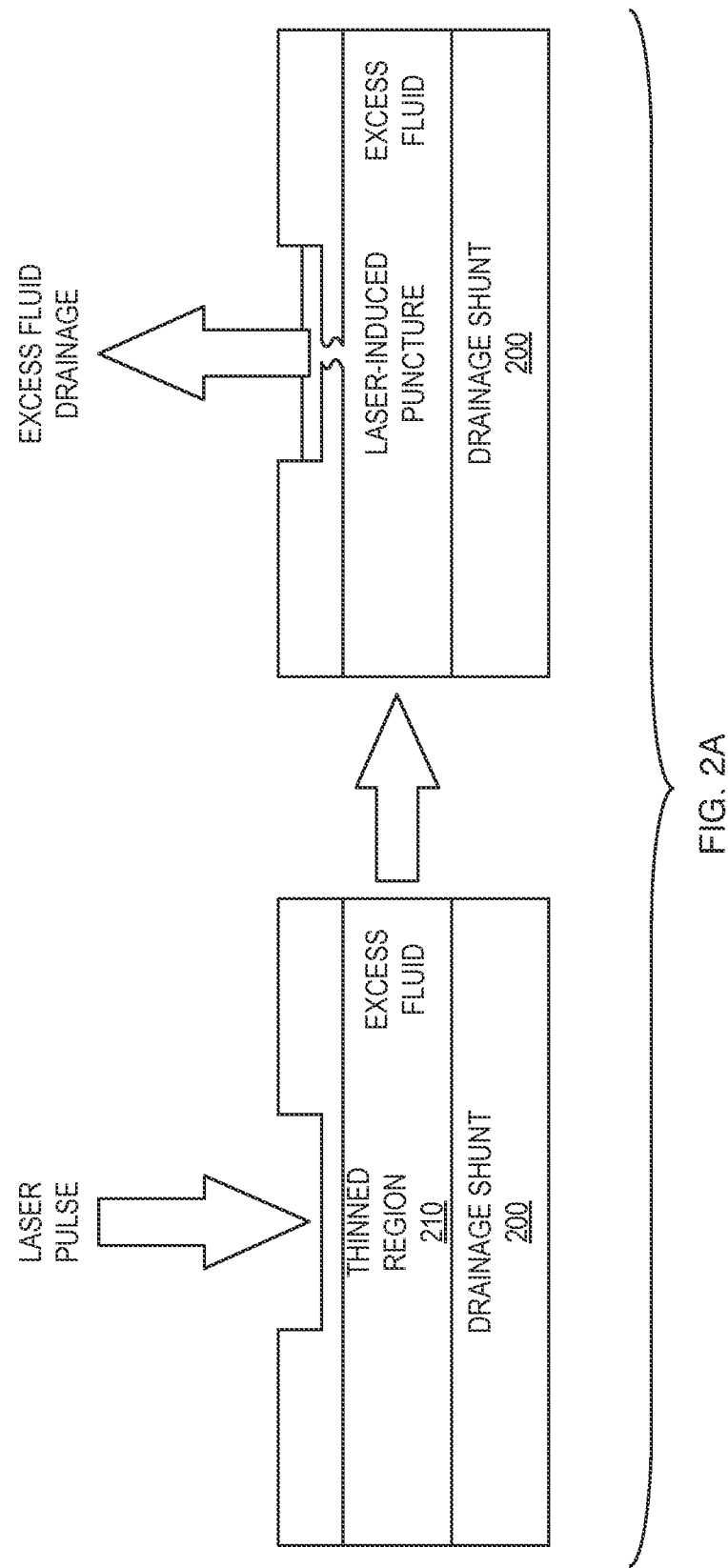

BASIC APPEARANCE

WITH SELF-LOCKING ARMS

SELF-LOCKING ARMS
+ HANDLING RING (NEXT TO OUTLET)

SACRIFICIAL PHOTORESIST COATING; OVERNIGHT HARDBAKING

1ST PARYLENE DEPOSITION AND PATTERNING (MASK #1)

1ST SACRIFICIAL PHOTORESIST COATING AND PATTERNING (MASK #2,3,4)
2ND PARYLENE DEPOSITION AND PATTERNING (MASK #5)

2ND SACRIFICIAL PHOTORESIST COATING AND PATTERNING (MASK #6)
3RD PARYLENE DEPOSITION AND PATTERNING (MASK #7)

3RD SACRIFICIAL PHOTORESIST COATING AND PATTERNING (MASK #8)
4TH PARYLENE DEPOSITION AND PATTERNING (MASK #9)

PHOTORESIST STRIPPING
5TH PARYLENE VACUUM SEALING DEPOSITION

IMPLANTABLE INTRAOCULAR PRESSURE DRAIN

CROSS-REFERENCE TO RELATED APPLICATIONS

This application is a Divisional of U.S. patent application Ser. No. 11/205,757, filed Aug. 16, 2005, which claims the benefit to and priority of U.S. Provisional Patent Application No. 60/602,110, filed Aug. 17, 2004, which are incorporated herein by reference.

STATEMENT AS TO RIGHTS TO INVENTIONS MADE UNDER FEDERALLY SPONSORED RESEARCH OR DEVELOPMENT

Work described herein has been supported, in part, by the National Science Foundation (Grant No. EEC-0310723). The United States Government may therefore have certain rights in the invention.

BACKGROUND OF THE INVENTION

Millions of people worldwide are afflicted by irreversible vision loss attributed to glaucoma. Over 3 million Americans are estimated to have glaucoma and approximately 120,000 are blind because of this disease.

There are often no signs or symptoms until vision loss is severe; estimates indicate that only half of the 3 million Americans with glaucoma are aware they have the disease. The cause of the disease is not well understood and there is currently no cure. Glaucoma is a chronic disease and must be treated for life.

Glaucoma is characterized by vision loss due to the damage of the optic nerve. Specifically, glaucoma is characterized by pathological changes in the optic disc and nerve fiber layer of retina.

One mechanism that can lead to damage of the optic nerve is the development of high intraocular pressure (IOP). Evidence from large, prospective studies suggests that reducing IOP to normal levels (15.5±2.6 mmHg (mean±SD)) reduces the rate of disease progression. Examples of such studies include Ethier et al., "Ocular biomechanics and biotransport," *Annu Rev Biomed Eng*, Vol. 6, pp. 249-73 (2004), and Schwartz and Budenz, "Current management of glaucoma," *Curr Opin Ophthalmol*, Vol. 15, pp. 119-26 (2004), both of which are incorporated by reference herein for all purposes.

Glaucoma management options include medical therapy, laser surgery, incisional surgery, and glaucoma drainage devices (GDDs). Medical therapy lowers IOP by improving the outflow of aqueous humor (AH) or to reduce its production. Some surgical techniques attempt to stimulate AH outflow, however, the primary surgical strategy is to manage glaucoma by lowering the patients' IOP through removal of excess AH. Regardless of the technique that is employed, accurate real-time measurements of IOP and the ability to restore normal levels are critical in the treatment of this disease.

Glaucoma management typically starts from interventions that are the safest and least invasive. Inasmuch, medical therapy is the most widely used treatment initially.

Although incurable, glaucoma can be treated with the aid of implant technology. Specifically, GDDs are used as a last resort in cases of refractory glaucoma or in patients who have not responded to previous treatment attempts. While GDDs can potentially lower IOP effectively, ophthalmologists are reluctant to use current GDDs due to high rates of complications.

Modern GDDs are based on the 1969 concept of the Molteno implant which consists of tube that shunts aqueous humor from anterior chamber to an external subconjunctival plate. Incorporated by reference herein for all purposes is Molteno, "New implant for drainage in glaucoma. Clinical trial," *Br J Ophthalmol*, vol. 53, pp. 606-15, (1969).

In the last 30-40 years, few innovative advances in surgical operation or implant devices have occurred. Only two major modifications to GDDs have been introduced: (1) addition of a valve to resist outflow and reduce hypotony and (2) increase in the endplate surface area to achieve lower IOPs.

GDDs are currently limited to the treatment of refractory glaucoma due to complications. The most significant complication of GDDs is postoperative hypotony (a condition where IOP is abnormally low, IOP<5 mmHg). During the early postoperative period, there is a lack of flow resistance prior to fibrous capsule formation around the end-plate resulting in hypotony, flat anterior chambers, choroidal effusions, and suprachoroidal hemorrhages. Strategies to avoid hypotony include performing the operation in two-stages to allow fibrous capsule formation, tube ligature, internal tube occlusion, and the development of valved GDDs. These solutions are not ideal and interestingly, conventional valved implants do not eliminate the occurrence of these complications. Furthermore, the success rate of current GDDs decreases by 10-15% every year suggesting poor long term performance.

Accordingly, improved devices and methods for treating glaucoma are highly desirable.

BRIEF SUMMARY OF THE INVENTION

A parylene tube shunt can be implanted to relieve intra-ocular pressure. The device is implanted with an open end in the anterior chamber of the eye, allowing excess fluid to be drained through the tube out of the eye. In one embodiment, only a first end of the tube implanted into the anterior chamber of the eye is open. Intra-ocular pressure (IOP) is then monitored, for example utilizing an implanted sensor. When IOP exceeds a critical valve, a practitioner intervenes, puncturing with a laser a thinned region of the tube lying outside the eye, thereby initiating drainage of fluid and relieving pressure. In accordance with alternative embodiments, the both ends of the tube are open, and the tube includes a one-way value configured to permit drainage where IOP exceeds the critical value. The tube may include projecting barbs to anchor the tube in the eye without the need for sutures.

An embodiment of an intra-ocular pressure drain in accordance with the present invention comprises a hollow tube comprising parylene and having an open end for implantation into an eye.

An embodiment of a method in accordance with the present invention for relieving intra-ocular pressure, comprises, providing a hollow tube comprising parylene and having an open end, implanting the open end of the hollow tube into an eye, and flowing fluid into the tube through the open end based upon a difference in ambient pressure and pressure within the eye.

An embodiment of a method in accordance with the present invention for fabricating an intra-ocular pressure drain, comprises, providing a workpiece comprising a sacrificial material, and depositing parylene to coat surfaces of the workpiece. The sacrificial material is removed to form a hollow parylene tube.

Various additional objects, features and advantages of the present invention can be more fully appreciated with reference to the detailed description and accompanying drawings that follow.

BRIEF DESCRIPTION OF THE DRAWINGS

FIG. 2A shows a simplified schematic view of the flow of fluid in the alternative embodiment of FIG. 2.

FIG. 11AA shows a simplified cross-sectional view of first check-valved inlet 1100 in a normally-closed mode.

FIG. 11AB shows a simplified cross-sectional view of second check-valved inlet 1102 in a normally-open mode.

DETAILED DESCRIPTION OF THE INVENTION

A parylene tube shunt can be implanted to relieve intra-ocular pressure. The device is implanted with an open end in the anterior chamber of the eye, allowing excess fluid to be drained through the tube out of the eye. In one embodiment, only a first end of the tube implanted into the anterior chamber of the eye is open. Intra-occular pressure (IOP) is then monitored, for example utilizing an implanted sensor. When IOP exceeds a critical valve, a practitioner intervenes, puncturing with a laser a thinned region of the tube lying outside the eye, thereby initiating drainage of fluid and relieving pressure. In accordance with alternative embodiments, the both ends of the tube are open, and the tube includes a one-way valve configured to permit drainage where IOP exceeds the critical value. The tube may include projecting barbs to anchor the tube in the eye without the need for sutures.

One embodiment of a glaucoma drainage device in accordance with the present invention comprises a tube with a passive check valve that permits fluid flow in only one direction—out of the eye. In addition, the exterior of the tube has mechanical barbs integrated at strategic positions that serve to anchor the device and prevent slippage after implantation. An alternate design includes thinned regions along the length of the tube that can be punctured using a laser to allow drainage.

Embodiments of an implantable tube shunt in accordance with the present invention can be used to treat patients with glaucoma. This device is implanted, exposing one end into the anterior chamber of the eye, to drain excess fluid out of the eye which is then absorbed by the body. Typically, such a device is used as an alternative to the natural drainage paths in the body which may malfunction due to clogging.

Various implementations of a glaucoma tube shunt are described here. A first design allows continuous drainage, and the second design permits drainage only after intervention is required as determined by a trained ophthalmologist.

Both designs are built around a simple implantable tube structure. This tube can be designed to have a bend in it at a designated position to facilitate implantation. Soft mechanical barbs are placed on the exterior of the tubes at strategic locations. These barbs serve to lock the tube in place once implanted, thus eliminating the need for sutures. Without these barbs, the tube is free to slide into and out of the eye through the incision made for implantation.

Figure 1:
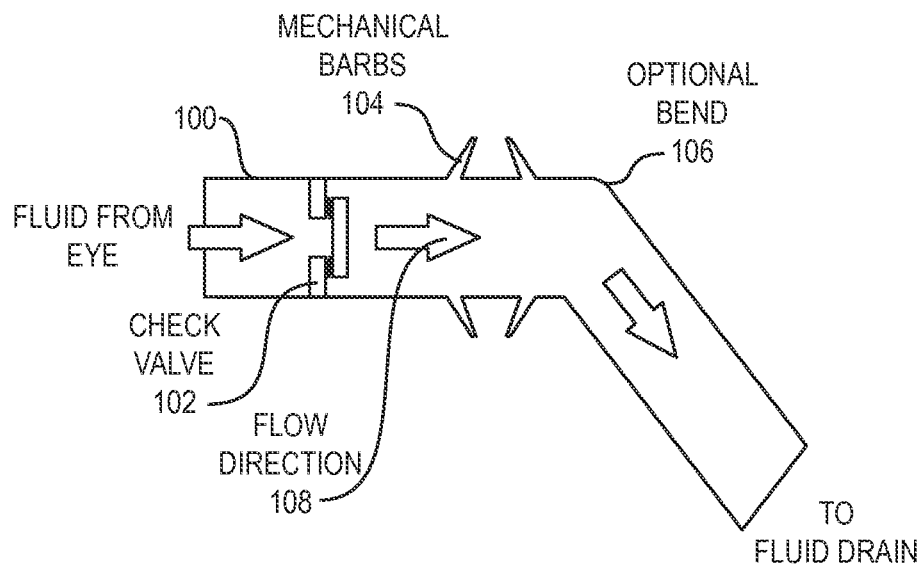
FIG. 1 shows a simplified cross-sectional view of one embodiment of a shunt in accordance with the present invention.

An embodiment of a continuous drainage shunt design is shown in FIG. 1. Continuous drainage shunt 101 comprises a tube 100 with both ends 100a-b open, one or more check valves 102, and mechanical barb structures 104 for anchoring. These check valves are integrated into the basic tube shunt to allow drainage whenever critical IOPs are reached without further intervention by an ophthalmologist.

Passive mechanical check valves 102 can be designed to open and close to target specific pressure ranges. Specifically, the check valve opens when the IOP reaches a designated critical value above which damage to the patient's optic nerve can happen. The opened check valve permits excess fluid to leak through the tube and out of the eye, reducing the IOP to safe levels. When drainage is sufficient to reduce the IOP below the critical value, the check valve closes, sealing the passageway and preventing any fluid from escaping the anterior chamber. This ability to drain only when dangerous IOPs exist is critical in ensuring that proper pressure is maintained in the eye and drainage is not excessive (possibly leading to hypotony). Particular embodiments of check valves and methods for their fabrication are detailed in U.S. provisional patent application No. 60/699,695, filed Jul. 15, 2005 and incorporated by reference herein for all purposes.

Specifically, in accordance with embodiments of this invention, a novel microfabricated back-to-back check-valved tube implant is may passively control the IOP regulation using a microfluidic scheme. The structural material is parylene C (poly-para-xylene C), a material that has demonstrated flexibility and biocompatibility for ocular MEMS devices. The device implantation is suture-less in order to achieve an economic and fast solution for releasing IOP.

The IOP regulation is employed by a microfluidic approach. Because elevated IOP is caused by blockage of intraocular fluid circulation, microfabricated check valves are here used to control the fluids flowing out of eye through a microchannel. The flow-pressure curves of check valves in FIGS. 7B and 7D show that for a normally-closed check valve, fluids cannot be passed unless the pressure is above the cracking pressure. For a normally-open check valve, fluid path is always open unless there is a sufficiently high backward pressure. A sophisticated passive pressure regulation is completed by combining these two kinds of check valves in back-to-back configuration, as shown in FIGS. 7E-F.

Figure 9A:
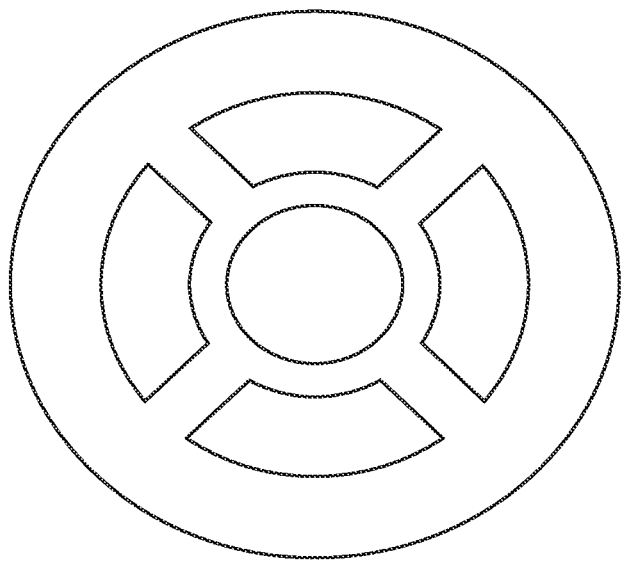
FIG. 9A shows a micrograph of one embodiment of a diagram in accordance with the present invention having straight-arm tethers.
Figure 9B:
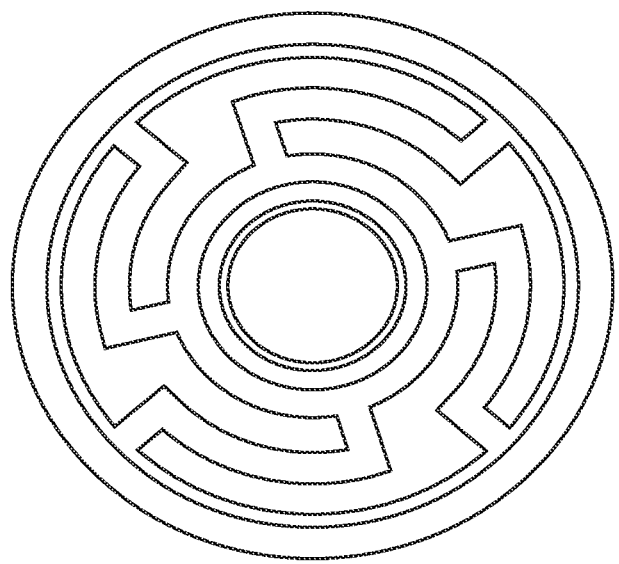
FIG. 9B shows a micrograph of another embodiment of a diaphragm in accordance with the present invention having twisted-arm tethers.
Figure 10:
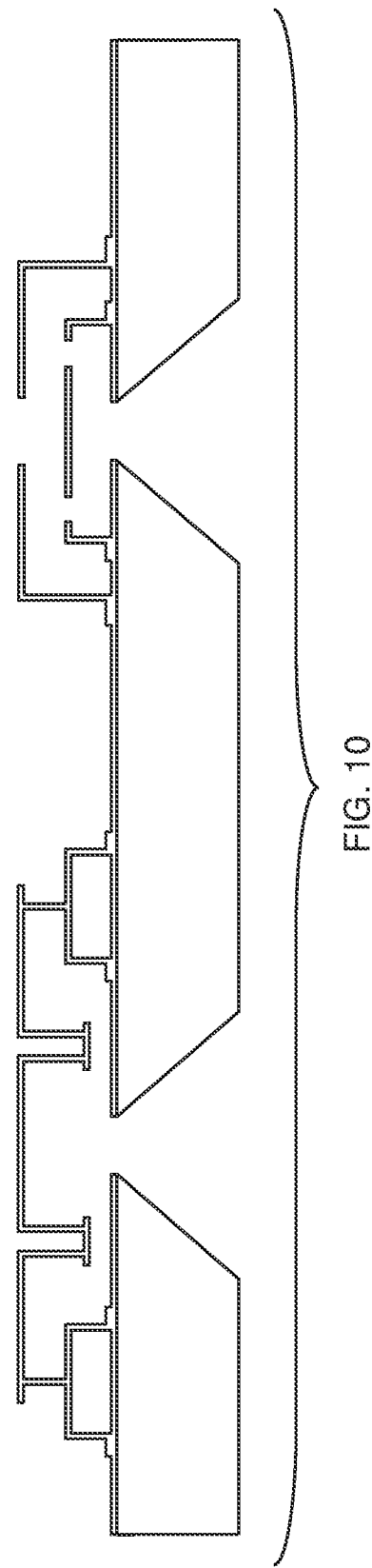
FIG. 10 shows a simplified cross-sectional view of normally-closed and normally-open check valves.

Micro check valves in accordance with embodiments of the present invention may be fabricated by a micromachining process. They are fundamentally free-standing diaphragms suspended by tethers. Depending on the load-deflection behavior of a circular membrane in FIG. 9A and designs of mechanical tethers in FIG. 9B, those diaphragms are systematically designed to change the flow resistance with respect to the fluidic pressure in a microchannel.

Figure 7A:
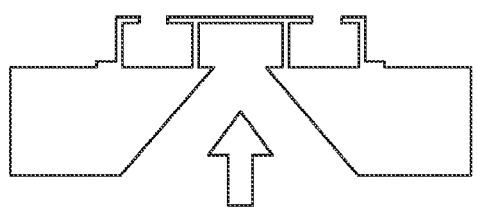
FIG. 7A is a simplified schematic view of a normally-closed check valve in accordance with an embodiment of the present invention.
Figure 7B:
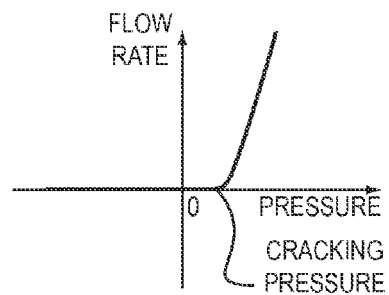
FIG. 7B plots flow rate versus pressure for the normally-closed check valve of FIG. 7A.
Figure 7C:
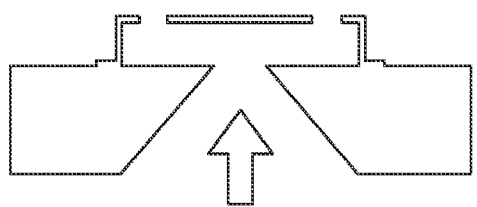
FIG. 7C is a simplified schematic view of a normally-open check valve in accordance with an embodiment of the present invention.
Figure 7D:
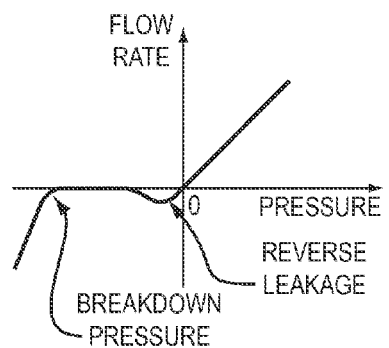
FIG. 7D plots flow rate versus pressure for the normally-open check valve of FIG. 7C.
Figure 7E:
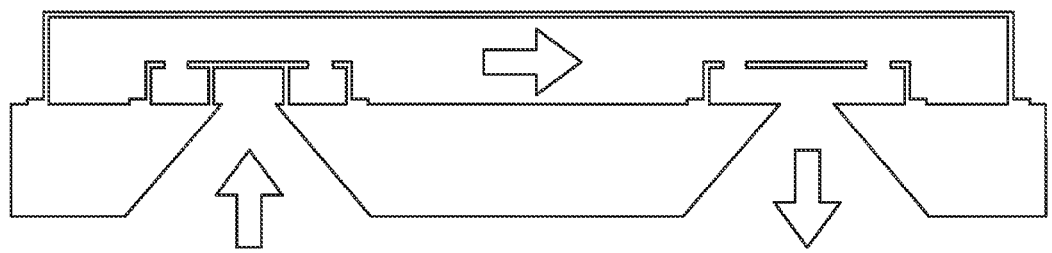
FIG. 7E is a simplified schematic view of a back-to-back configuration in accordance with an embodiment of the present invention of a normally-open and a normally-closed check valve.
Figure 7F:
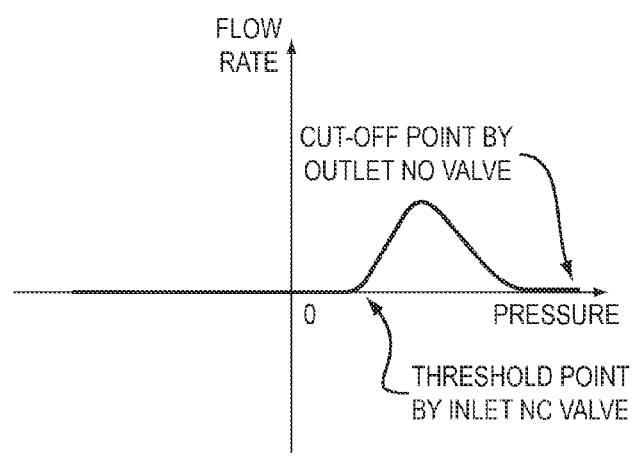
FIG. 7F plots flow rate versus pressure for the configuration of FIG. 7E.
Figure 8:
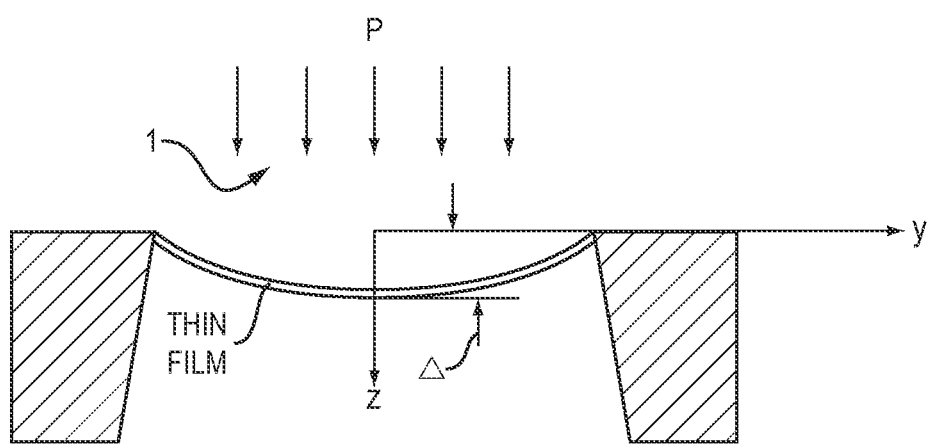
FIG. 8 shows a simplified schematic view of one embodiment of a diaphragm.

FIGS. 7A and 7C show the designs of a normally-closed and a normally-open micro check valve, respectively. Vacuum-collapsed sealing is used to realize the operation of normally-closed check valve. By creating the pressure difference between vacuum chamber and environment, the top wall 700 is collapsed, which provides the pre-stressing force for the membrane 702 to have dynamic behavior of a normally-closed check valve as in FIGS. 7A-B.

$$P = C_1 \frac{\sigma t W_0}{R^2} + C_2 \frac{\sigma t W_o^3}{R^4}, \text{ where}$$

$P$ = Uniform pressureload $W_o$ = Membrane deflection $R$ = Radius of circular membrane $t$ = Membrane thickness $\sigma$ = Residual stress of material; and $C_1$ and $C_1$ are constants.

Figure 11A:
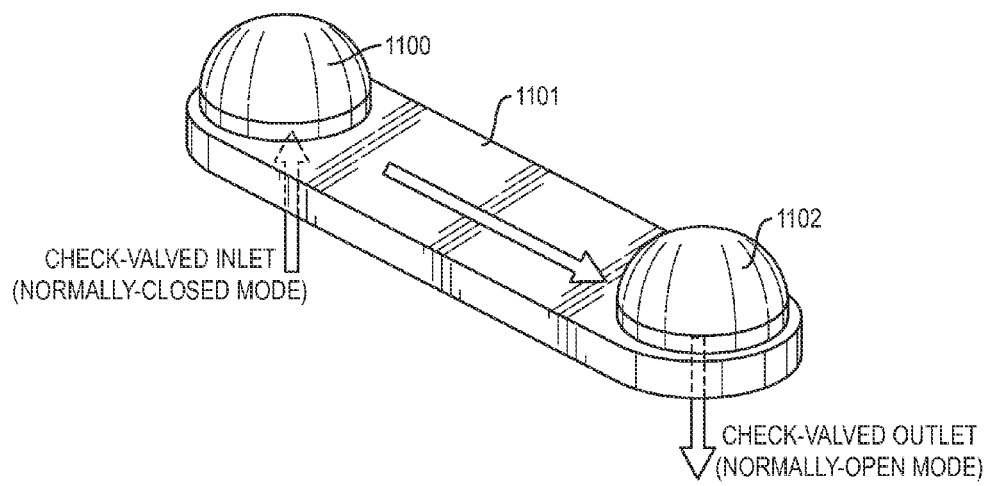
FIG. 11A shows a simplified schematic view of valve operation of one embodiment of a shunt device in accordance with the present invention.
Figure 11A:
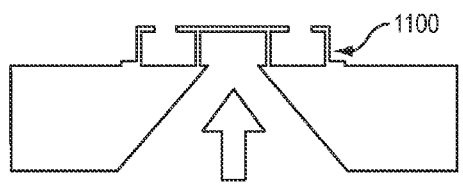
Figure 11A:
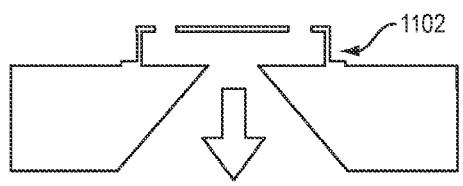
Figure 11B:
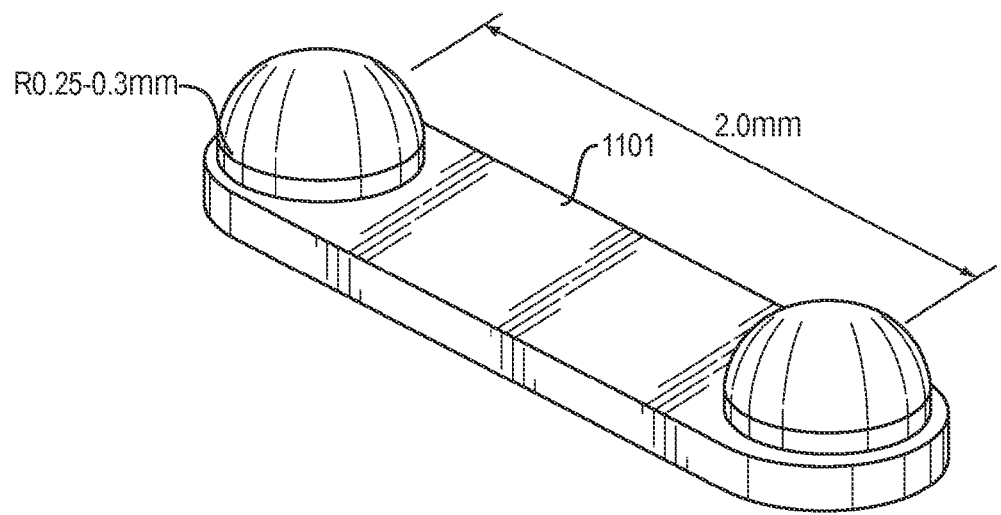
FIG. 11B shows a simplified top perspective view showing dimensions of one embodiment of an implantable shunt in accordance with the present invention.
Figure 11C:
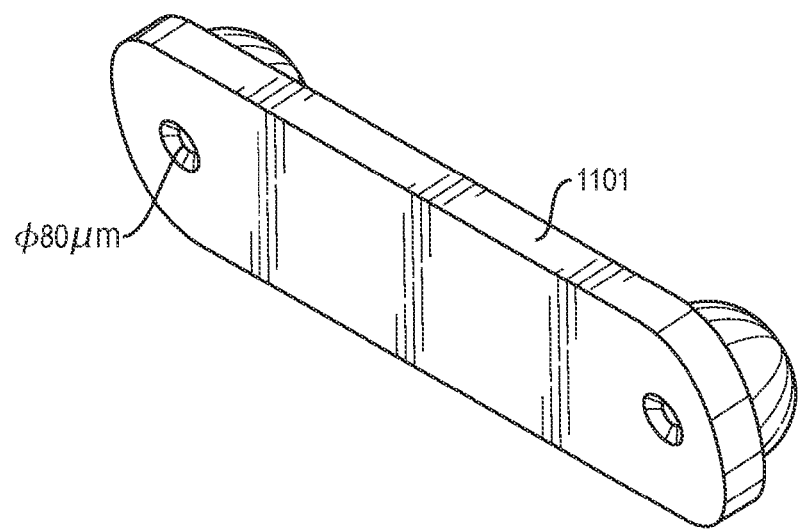
FIG. 11C shows a bottom perspective view of the embodiment of the implantable shunt shown in FIGS. 11A-B.

The back-to-back check-valved configuration is incorporated in a tube enclosure as in FIGS. 11A-C for implantation. FIG. 11A shows a simplified schematic view of valve operation of one embodiment of a shunt device 1101 in accordance with the present invention. FIG. 11AA shows a simplified cross-sectional view of first check-valved inlet 1100 in a normally-closed mode. FIG. 11AB shows a simplified cross-sectional view of second check-valved inlet 1102 in a normally-open mode. FIG. 11B shows a simplified top perspective view showing dimensions of one embodiment of an implantable shunt in accordance with the present invention. FIG. 11C shows a bottom perspective view of the embodiment of the implantable shunt of FIGS. 11A-B.

Figure 12:
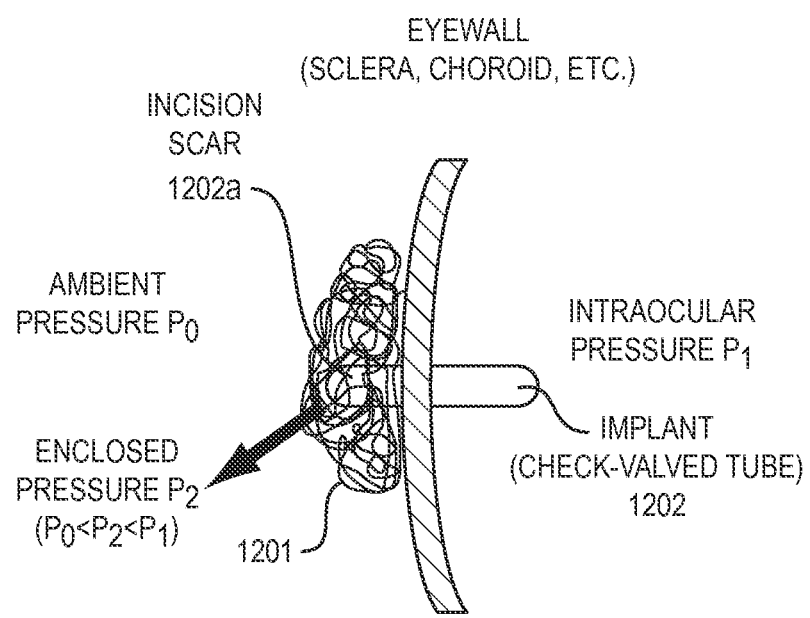
FIG. 12 shows a simplified schematic view of operation of an embodiment of an implantable shunt in accordance with the present invention.

The concept of the implantation operation is illustrated by FIG. 12. By creating an appropriately-sized incision, the implant can be inserted across the eye-wall, sclera, choroids, etc. The incision damage will be naturally healed, and any resulting minor scarring 1200 encloses one end 1202a of the implant 1202 with some pressure ($P_2$). This enclosed pressure $P_2$ has been confirmed to be lower than intraocular pressure ($P_1$) and higher than ambient pressure ($P_0$). Therefore, intraocular fluids can be passively controlled to flow through the back-to-back check-valved implant 1202 and evaporate/diffuse away from the scar to realize IOP drainage.

Figure 13A:
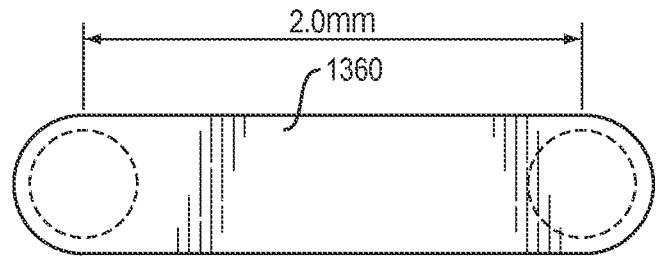
FIG. 13A shows a top view of one embodiment of an implantable shunt in accordance with the present invention.

The shape of the tube enclosure can be optimized for implantation feasibility. Different geometrical designs have been developed in FIGS. 13A-C. The first design 1360 of FIG. 13A simply has the basic enclosure in appearance.

Figure 13B:
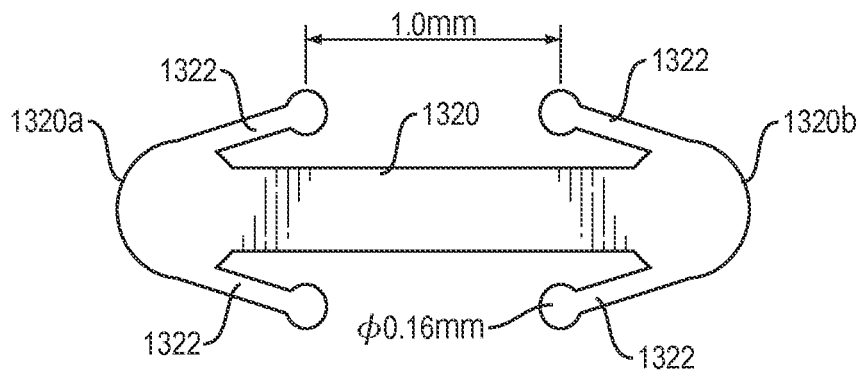
FIG. 13B shows a top view of an alternative embodiment of an implantable shunt in accordance with the present invention.

The second design 1320 of FIG. 13B has self-locking arms 1322 which confine two ends 1320a-b of the tube implant 1320 at the inside and outside of the eye in order to keep the implant functional. Because these self-locking arms are made of flexible structural materials, they can be folded to fit through the incision hole during implantation and restored to the original positions as well as anchor the implant across the eyewall afterwards.

Figure 13C:
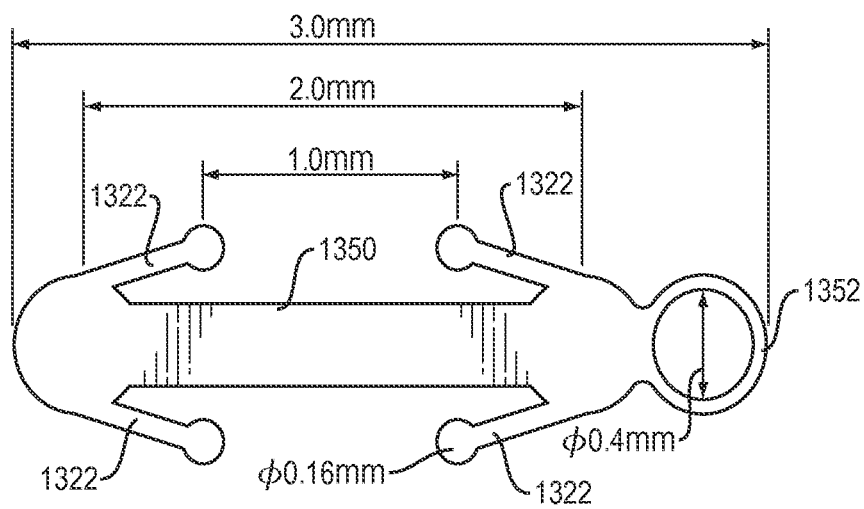
FIG. 13C shows a top view of another alternative embodiment of an implantable shunt in accordance with the present invention.

In the last design shown in FIG. 13C, the implant 1350 has a handling ring 1352 for any carrying/surgery convenience and is a structure that prevents rotation from the optimal position. This design 1350 also includes the self-locking arms 1322.

The method of manufacturing the invention is a multi-layer surface micromachining process in order to fabricate flexible ("skin") device implant. It is an all-polymer process which has photoresist and parylene C as materials. An embodiment of a process flow for fabricating an implant in accordance with an embodiment of the invention is shown in the simplified cross-sectional views of FIGS. 14(a)-(f). The typical process steps are given as follows.

Figure 14A:
FIGS. 14A-F show simplified cross-sectional views illustrating steps for fabricating an implantable shunt in accordance with an embodiment of the present invention having check valves.
Figure 14B:

FIG. 14A shows spin-coating photoresist 1400 as the first sacrificial layer, followed by overnight hardbaking. FIG. 14B shows depositing parylene C 1402 as the first structural layer.

Photoresist is spin-coated, and patterned by photolithography. The pattern is transferred on parylene C 1402 by oxygen plasma etching.

Figure 14C:
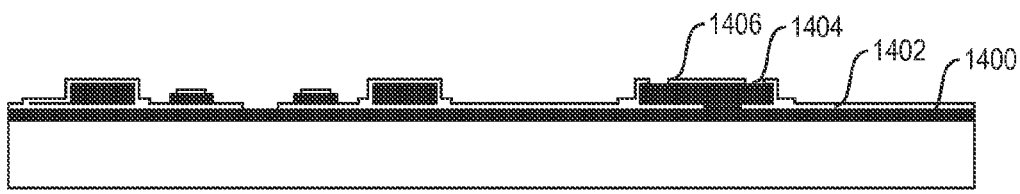

FIG. 14C shows spin-coating of photoresist 1404 as the second sacrificial layer and patterning of the photoresist by photolithography employing three successive masking steps (mask #s 2-4). FIG. 14C also shows depositing parylene C as the second structural layer 1406, followed by patterning this second structural layer with another mask (mask #5).

Figure 14D:
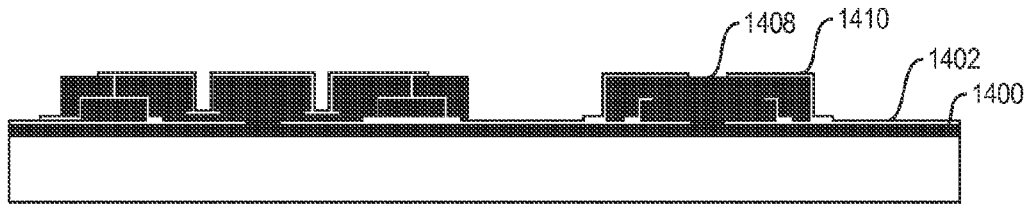

FIG. 14D shows spin-coating photoresist 1408 as a second sacrificial layer, and the patterning of photoresist (mask #6) by photolithography. FIG. 14(d) also shows the patterning of parylene C 1410 by oxygen plasma etching under another photoresist mask (mask #7).

Figure 14E:
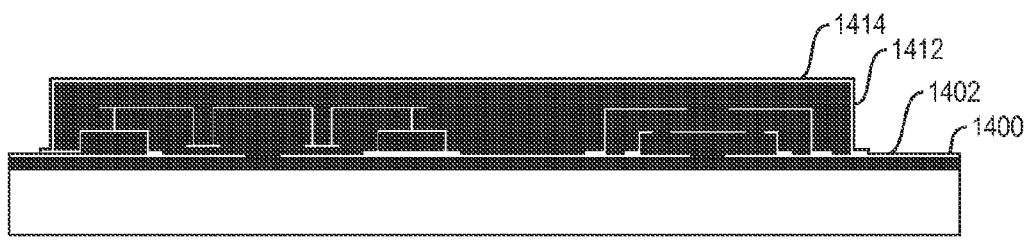

FIG. 14E shows spin-coating photoresist 1412 as the third sacrificial layer and the patterning of photoresist (mask #8) by photolithography. FIG. 14(e) also shows the patterning of parylene C 1414 as the third structural layer under another photoresist mask (mask #9).

Figure 14F:
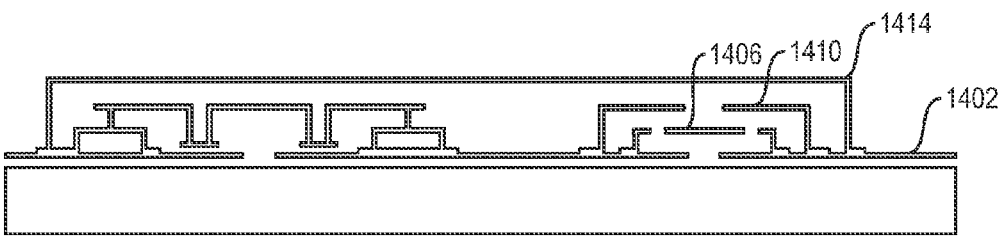

FIG. 14F shows dissolving the photoresist to release the flexible device by acetone dip and isopropyl alcohol/deionized water rinse. Parylene C is deposited as the fifth structural layer for final vacuum sealing. In this last step of the fabrication process, vacuum sealing is satisfied because the deposition pressure of parylene C is sufficiently low (~22 mTorr). It provides enough pressure difference for the chambers of normally-closed check valve to be collapsed. Because the structural layers are all made out of parylene C, the device invention is flexible and implantable.

Previous research has focused on releasing IOP for glaucoma treatment. Embodiments in accordance with the present invention use microfluidic passive elements to effectively and reliably perform IOP drainage. The back-to-back check-valved configuration can passively control IOP without any electronic device, so the device invention completely meets the biocompatibility requirement by using parylene C as an implantable structural material.

A number of variations and modifications are possible. For example, the threshold pressure that activates IOP drainage of implant can be varied by mechanical designs of inlet check valve. Moreover, the cutoff pressure that shunts IOP drainage of implant can be varied by mechanical designs of outlet check valve. Furthermore, the shape of tube implant can be changed to further facilitate clinical implantation.

Fabrication process of the implant can be changed to make on-substrate devices instead of flexible ones, for the ease of on-bench microfluidic coupling and testing prior to implantation. Fabrication process of the implant can be changed depending on specific implantation requirements.

In accordance with still other embodiments, structural material of the implant can be changed depending on specific fabrication or implantation request. Number and configuration of valves can also be changed depending on specific implementation.

Embodiments in accordance with the present invention incorporate a number of innovative features. One such feature is the use of back-to-back check-valved configuration for passive pressure regulation, Another innovative feature is the design of the inlet (normally-open) and the outlet (normally-closed) check valves of the device implant.

Still other innovations offered by certain embodiments in accordance with the present invention include the implantation strategy for realizing suture-less implantation; the design of the shape of check-valved tube for facilitating clinical implantation; selection of material to fabricate the flexible and biocompatible device implant; and design of the micromachining process to fabricate the flexible device implant.

The following papers are incorporated by reference herein for all purposes: X.Q. Wang et al., "A Parylene Micro Check Valve," Technical Digest, The 12th IEEE International Conference on MicroElectroMechanical Systems (MEMS1999), Orlando, Fla., USA, Jan. 17-21, 1999, pp. 177-182; X.Q. Wang and Y.-C. Tai, "A Normally Closed In-Channel Micro Check Valve," Technical Digest, The 13th IEEE International Conference on MicroElectroMechanical Systems (MEMS2000), Miyazaki, Japan, Jan. 23-27, 2000, pp. 68-71; C.T. Loy et al., "A series solution approach to an analytical load-deflection relation for the measurement of mechanical properties of thin films," Journal of Micromechanics and Microengineering, vol. 9, 1999, pp. 341-344; and E. Meng et al., "Implantable Parylene MEMS for Glaucoma Therapy," Technical Digest, The 3rd IEEE EMBS Special Topic Conference on Microtechnologies in Medicine and Biology (EMBS-MMB2005), Oahu, Hi., USA, May 12-14, 2005.

Figure 2:
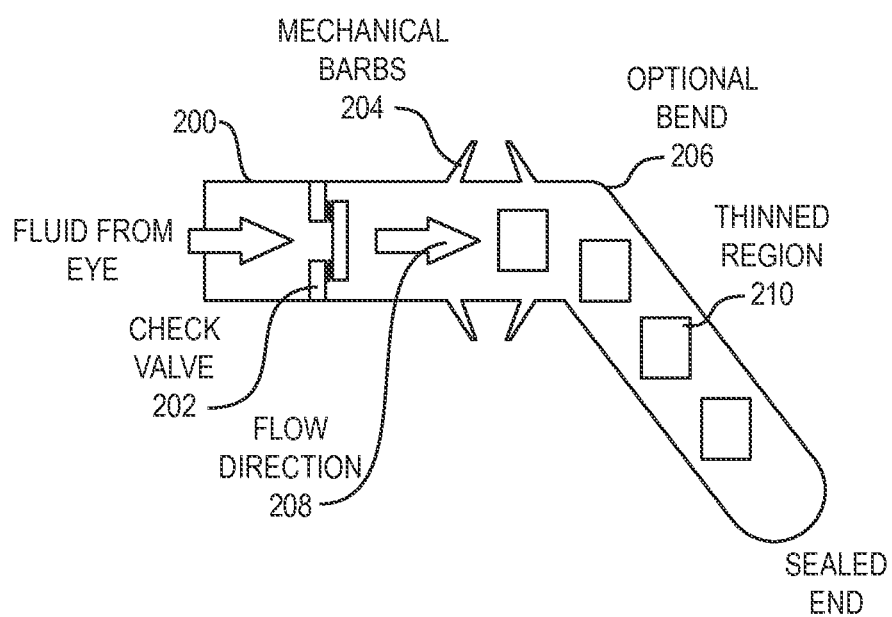
FIG. 2 shows a simplified cross-sectional view of an alternative embodiment of a shunt in accordance with the present invention.

An alternative to the continuous drainage shunt shown in FIG. 1, allowing an ophthalmologist to determine when to initiate drainage, also exists. FIG. 2 shows a simplified cross-sectional view of such an alternative embodiment. Instead of a tube with both ends open, here one end 200b is shut. Only the end 200a of the tube 200 which implanted into the anterior chamber is open. In order to initiate drainage, thinned regions 210 along the length of the tube are created.

FIG. 2A shows a simplified schematic diagram illustrating the mechanism of AH release through laser-induced punctures in thinned regions. As shown in FIG. 2A, these thinned regions 210 can be punctured by applying a laser pulse. In the particular embodiment shown in FIG. 2, check valve 202 is also included to prevent backflow of fluid into the eye.

Incorporated by reference herein for all purposes is U.S. nonprovisional patent application Ser. No. 11/148,124, filed Jun. 7, 2005. This application describes an intra-ocular pressure sensor that could indicate IOP to a health provider, allowing for intervention by the health provider to puncture the tube with a laser pulse in accordance with an embodiment of the present invention.

Both of the embodiments of tube shunt designs previously discussed may be fabricated using Parylene C. Tubes are formed by depositing Parylene around a sacrificial material that defines the tube shape. The check valve and mechanical barbs can also be formed at this time. If necessary, photolithographically defined regions of the parylene tube are thinned down by plasma etching. FIGS. 4A-J details the basic fabrication process for the drains. Slight modifications to the layout and process will result in the various versions described here.

Figure 4A:
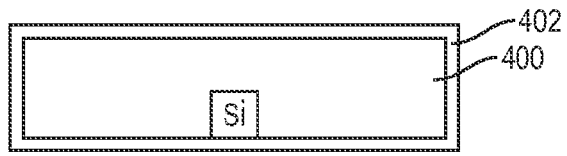
FIG. 4A-J shows simplified cross-sectional views of the steps of fabricating a tube shunt structure in accordance with an embodiment of the present invention.

FIGS. 4A-4J show simplified cross-sectional views of the steps of fabricating a drain structure in accordance with one embodiment of the present invention. In FIG. 4A, silicon workpiece 400 is exposed to thermal oxidizing conditions, such that oxide layer 402 is grown on all surfaces.

Figure 4B:
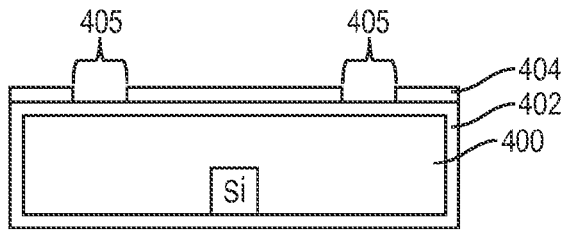
Figure 4C:
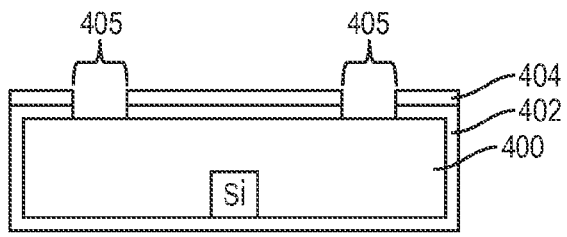

FIG. 4B shows the next step in the process flow, wherein a photoresist mask 404 is patterned over oxide 402 on top surface 400a, exposing gaps 405. In the step illustrated in FIG. 4C, portions of oxide layer 402 underlying gaps 405 are removed by etching selective to the underlying silicon workpiece 400.

Figure 4D:
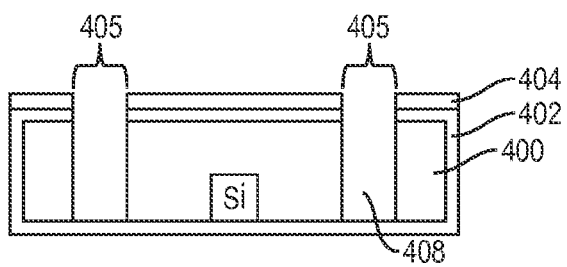

FIG. 4D shows changing of etching conditions to etch trenches 408 extending all the way through the entire silicon workpiece 400 in gap regions 405 exposed by mask 404, to stop an oxide 402 present on the backside of the workpiece. In this manner, the shape of the beam of sacrificial material, and hence of the tube that is to be formed around it, is defined. The location and size of projecting barbs may also be defined during this step, by controlling the shape of the outline of the etched silicon beam.

Figure 4E:
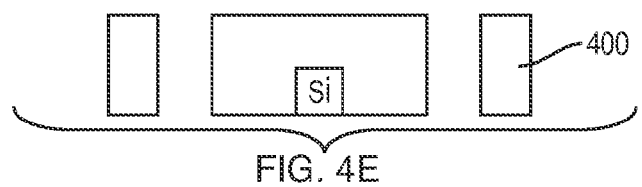
Figure 4F:
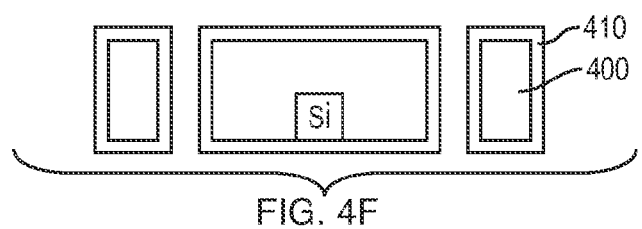
Figure 4G:
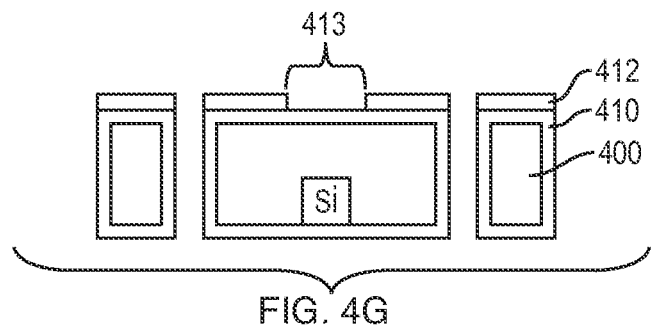

FIG. 4E shows stripping of the photoresist mask and removal of the oxide from all remaining surfaces of the workpiece. FIG. 4F shows the next step, wherein the silicon workpiece bearing the etched trenches is subjected to parylene deposition conditions oxidizing conditions resulting in the formation of parylene 410 on exposed surfaces of the workpiece. FIG. 4G shows the next step, wherein a second photoresist mask 412 is patterned over selected portions of parylene-coated workpiece, exposing gaps 413.

Figure 4H:
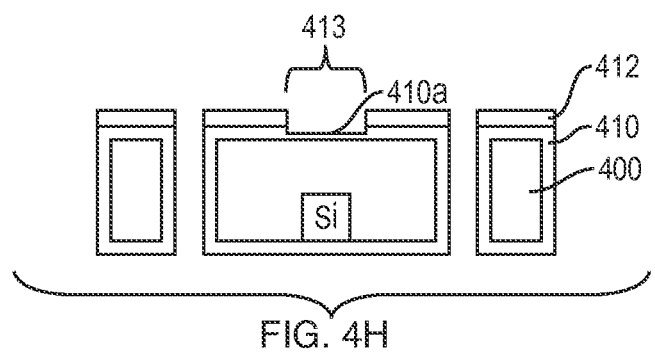

FIG. 4H shows the following step, wherein the parylene layer 410 is partially removed in unmasked regions 413, thereby creating thinned wall 410a of the drain structure. Conditions such as a timed oxygen plasma etch in a plasma etcher, reactive ion etcher, deep reactive ion etcher, or similar dry etching apparatus can be employed under timer conditions for this partial parylene etching step.

Figure 4I:
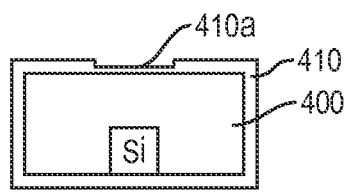

FIG. 4I shows separation of the shunt from the etched wafer. This can be achieved by an automated cutting apparatus such as a dicing saw. Alternatively, the shunt can be manually separated from the etched wafer by cutting through the parylene with a sharp knife or razor blade, then using a diamond scribe to score and then break the sacrificial silicon beam contained within the shunt.

Figure 4J:
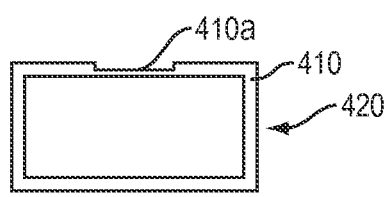

FIG. 4J shows the removal of the sacrificial silicon from the interior of the drain structure through the open ends, creating a hollow drain member for carrying fluid away from the eye. Silicon is removed by immersing the shunt into a wet chemical etchant bath. Many suitable chemistries exist for removal of this sacrificial material including hydrofluoric acid-nitric acid-acetic acid (HNA) treatment.

Figure 3A:
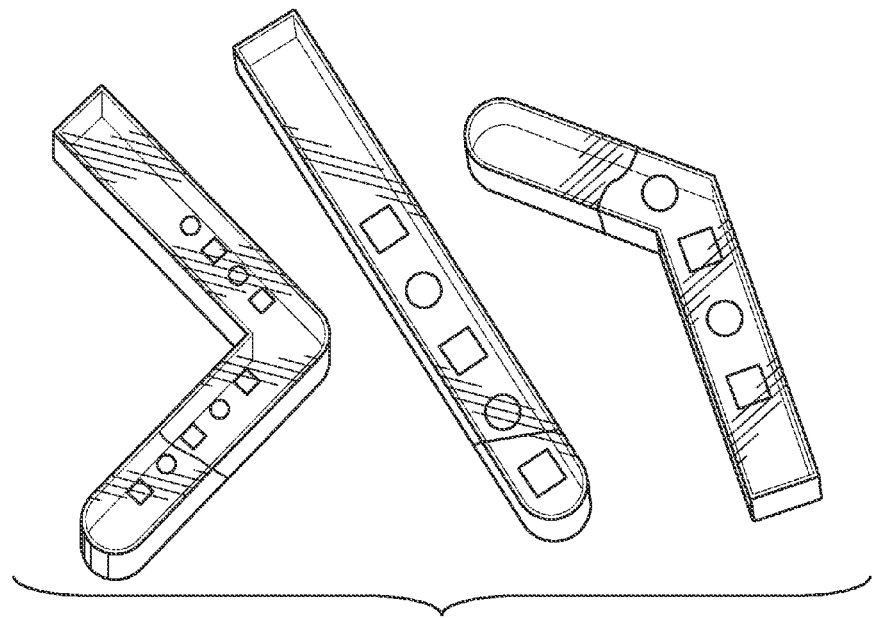
FIGS. 3A-3B show photographs of tube shunt structures in accordance with embodiments of the present invention.

FIG. 3A shows three fabricated drains with different geometries and thinned region designs. The silicon support is the darker area near the rounded (closed) tip and is not completely removed.

Certain embodiments in accordance with the present invention fabricate a complete GDD or a passive IOP sensor using MEMS technology. MEMS technology offers several advantages over traditional approaches to glaucoma therapy including highly functional microfluidic systems that can be adapted to drug delivery and IOP management; miniaturized sensors suitable for implantation with precise and accurate readouts. Precision and batch fabrication of MEMS devices are discussed by Mokwa and Schnakenberg, "Micro-transponder systems for medical applications," *IEEE Transactions on Instrumentation & Measurement*, vol. 50, pp. 1551-5 (2001), incorporated by reference herein for all purposes.

One purpose of a GDD is to control and regulate IOP. However, conventional GDDs are lacking in function and in efficacy. These factors are partly attributed to suboptimal design and nonideal biomaterial selection. By leveraging polymer MEMS technology in accordance with embodiments of the present invention, the components necessary for a GDD can be seamlessly integrated into a miniaturized, single-piece device that is biocompatible and minimizes complications. An embodiment of a MEMS GDD in accordance with an embodiment of the present invention is an implantable, passive parylene shunt to reduce and regulate IOP by controlling the removal of excess aqueous humor from the anterior chamber.

Until now, MEMS pressure sensors designed for the purpose of IOP sensing required electrical circuitry and hermetic sealing which severely limits their implementation. Also, tonometers fabricated using conventional techniques are not suitable for continuous IOP monitoring and cause a considerable amount of patient discomfort. They typically require contact with a patient's cornea, necessitating the use of anesthetics. We propose a new mechanical sensing paradigm for a passive and biocompatible parylene MEMS IOP sensor. Our sensor will be integrated with novel parylene/silicon tissue anchors such that the sensor platform will be implanted behind the cornea and attached to the iris without sutures. The mechanical structure has an integrated indicator tip that can be monitored through external optics to track changes in IOP.

Parylene is selected as the structural material for its desirable properties, both as a biomaterial and a MEMS material. It is a USP Class VI material that is utilized for its biocompatibility, biostability, and low cytotoxicity. Parylene is a proven MEMS material, as evidenced at least by the following references, each of which is incorporated by reference herein for all purposes: Wang and Tai, "A Normally Closed In-Channel Micro Check Valve," in *MEMS* 2000. Miyazaki, Japan (2000); Xie et al., "Integrated Electrospray Chip for Mass Spectrometry," in *mTAS* 2002. Nara, Japan pp. 709-711 (2002); Xie et al., "Integrated Surface-Micromachined Mass Flow Controller," in *MEMS* '03. Kyoto, Japan (2003); He et al., "Parylene Neuro-Cages for Live Neural Networks Study," in *Transducers* 2003. Boston, Mass., pp. 995-998 (2003); Meng, "High Aspect Ratio Parylene Etching for Microfluidics and BioMEMS," in *Micro Total Analysis Systems* 2004, vol. 2. Malmo, Sweden, pp. 401-3 (2004); Meng and Tai, "Polymer MEMS for Micro Fluid Delivery Systems," in *Polymer Preprints*, vol. 44. New York, N.Y., pp. 552-553 (2003).

Parylene has excellent properties including low process temperature, low defect density, transparency, and chemical inertness. In addition, parylene technology accommodates multi-layer processing to produce highly functional structures and features. While biological environments are extremely corrosive to most MEMS materials, parylene is not affected as it cannot be degraded hydrolytically. See Kroschwitz, "Kirk-Othmer Encyclopedia of Chemical Technology," Fourth ed. New York: John Wiley & Sons, Inc. (1998), incorporated by reference herein for all purposes.

The combination of an implantable MEMS sensor and drain will make it possible to closely track a patient's IOP history and maintain IOP at normal levels. This comprises a novel and complete diagnostic and therapeutic system for treating glaucoma.

GDDs are designed to incorporate several physiological parameters. Aqueous humor is produced in the eye at 2.4±0.6 µL/min (mean±SD) and changes over the course of a day (morning: 3.0 µL/min; afternoon: 2.4 µL/min; evening: 1.5 µL/min). The resistance of conventional AH drainage tissues is ~3-4 mmHg/µL/min. The minimal system requirements for a MEMS GDD are a shunt and pressure-sensitive valve to remove excess AH such that IOP is maintained between 5-22 mmHg.

A parylene shunt in accordance with embodiments with the present invention has been fabricated using a sacrificial silicon technology. As described above in connection with FIGS. 4A-J, a shunt mold is etched into a silicon wafer and parylene is deposited around the mold. Each shunt is removed from the master mold and the silicon is chemically removed.

Figure 3B:
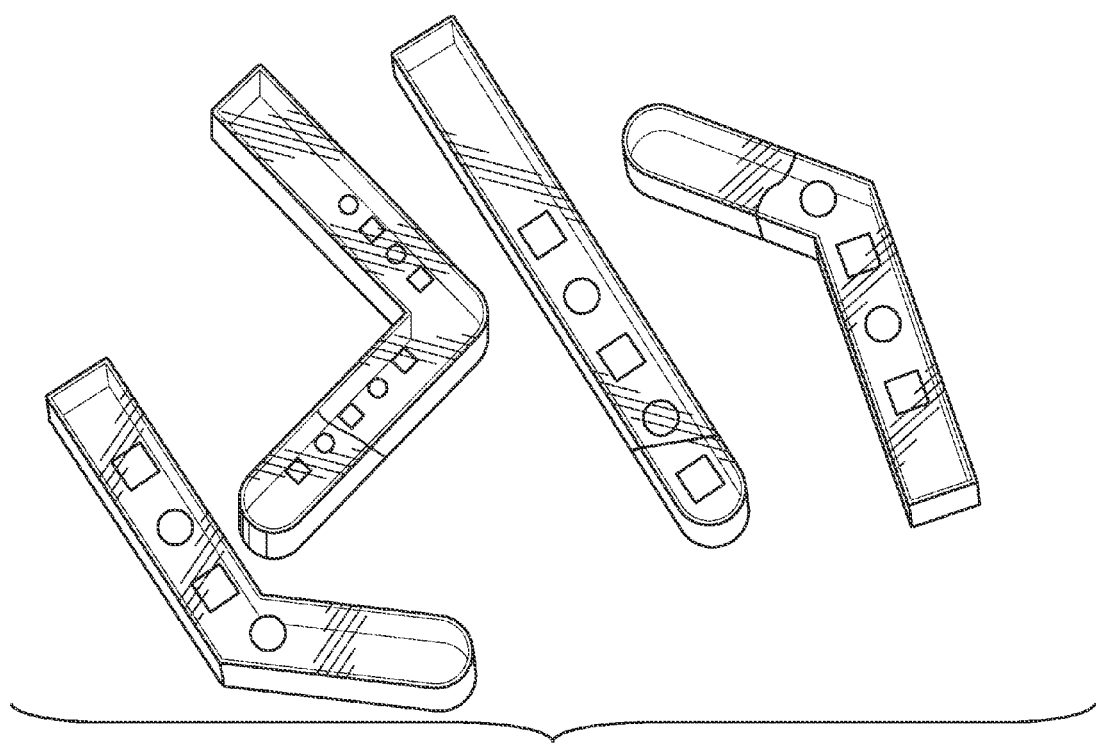

FIG. 3B shows Parylene shunts with and without thinned regions. The dark region at the rounded tip is silicon that has been left to provide contrast for viewing. In FIG. 3B, several types of shunts are shown with one end sealed off (~8×0.5×1 mm3 and 10 µm thick wall). At the sealed-ends, remnants of the silicon mold are visible. This closed end is implanted into the anterior chamber of the eye where it comes into contact with AH. At this end of the shunt are several regions where the parylene has been etched down to 0.5 µm or less. When elevated IOP is detected these thinned regions can be punctured using a laser to allow excess AH to be released from the anterior chamber. Flow and pressure regulation is achieved by controlling the number of and time at which the punctures are made along the closed end of the shunt.

Like some conventional GDDs, the parylene device in accordance with the embodiments of the present invention shown in FIG. 3B does not prevent bi-directional flow. However, the laser puncture feature does allow flexibility in initiating treatment. Alternative designs in accordance with the present invention can integrate a check valve to enforce one-way flow and mechanical barbs on the exterior of the tube to anchor the device and prevent slippage after implantation. Preliminary evaluation of these shunts by implantation into rabbit eyes may also suggest the need for increased stiffness to facilitate handling and surgical insertion of these delicate tubes.

At physiological flow rates, pressure drops are negligible for the size of the shunt. Therefore, the majority of the pressure drop in the system will be concentrated at the valve.

In order to promote drainage of AH out of the anterior chamber, the valve should be optimized to drain at a flow rate equal to the production of AH at elevated IOPs. It must open at IOP>22 mmHg and close when IOP≤22 mmHg to prevent hypotony.

Conventional GDDs with valves have been unable to perform the shut-off function required after desired IOP levels are met. It is suspected that once the conventional valves open, they never close and possibly account for some of the observed complications.

In "A Check-Valved Silicone Diaphragm Pump," in *MEMS* 2000. Miyazaki, Japan (2000), incorporated by reference herein for all purposes, Meng et al. demonstrated a parylene valve that can be adapted to meet all the requirements for application to GDDs. A new biocompatible, pressure sensitive valve in accordance with an embodiment of the present invention based on this design will enable advanced glaucoma management by maintaining healthy IOP levels and achieving pressure-regulated shut-off.

A mechanical pressure sensor for use in embodiments in accordance with the present invention is based on the principle of operation of a Bourdon tube. Incorporated by reference herein is Clark and Reissner, "Deformations and stresses in bourdon tubes," *Journal of Applied Phyics*, vol. 21, pp. 1340-1 (1950).

Figure 5:
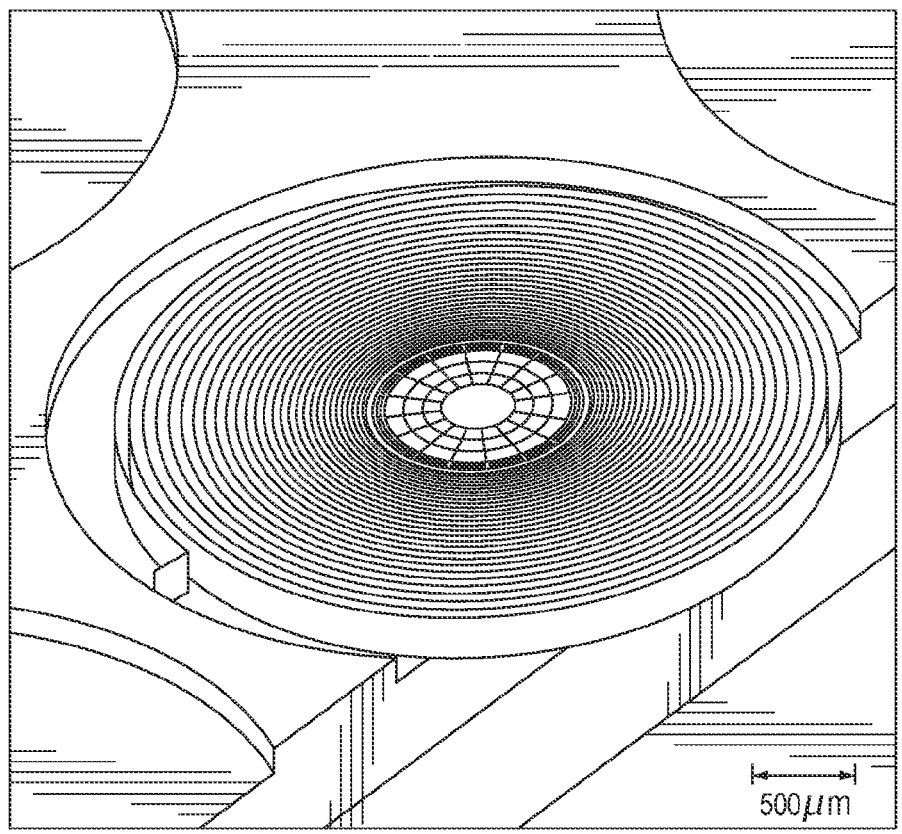
FIG. 5 shows a scanning electron micrograph (SEM) of a spiral-tube parylene IOP sensor, in accordance with an embodiment of the present invention.
Figure 5A:
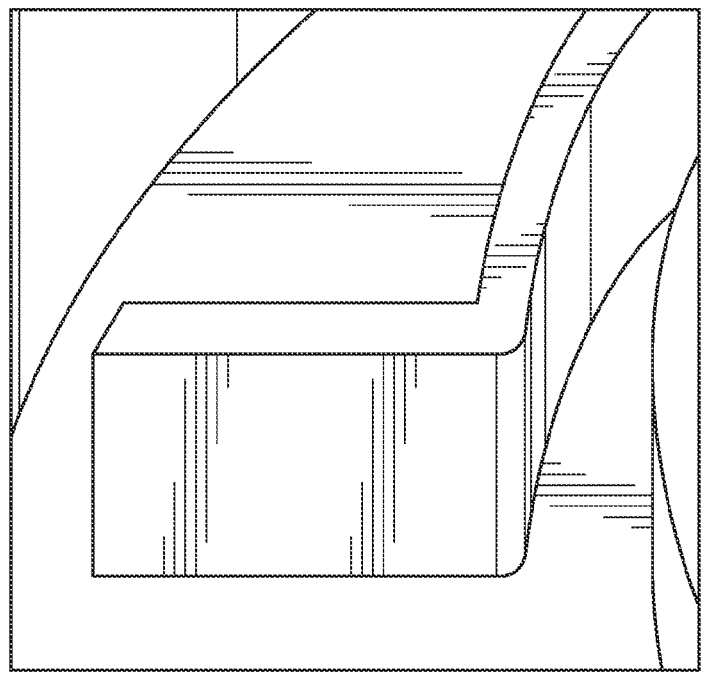
FIG. 5A shows an enlarged SEM of the integrated indicator tip of the IOP sensor shown in FIG. 5.

FIG. 5 is a SEM of passive, spiral-tube parylene IOP sensor (1 mm radius) for use in accordance with embodiments of the present invention. FIG. 5A is a close-up of integrated indicator tip (6×100 μm) of the sensor shown in FIG. 5. Pressure sensor 500 comprises a centrally supported, free-standing parylene spiral-tube 502 formed by a long, thin-walled toroidal channel. Indicator tip 504 is integrated at the end of the channel at the circumference of the spiral as a means for simple optical readout. In "Spiral-Tube Parylene Intraocular Pressure Sensor," in *MEMS* 2005. Miami, Fla., pp. 311-4 (2005), incorporated by reference herein for all purposes, Chen et al. report the fabrication of such a device.

The hollow spiral channel forming the sensor is sealed at 1 Atm as the gauge reference. When a uniform pressure difference is generated across the channel walls, a bending moment is created forcing an in-plane radial and angular deformation of the tube. When the external pressure is lower than the internal pressure in the channel, the spiral structure unwinds. When the external pressure exceeds the internal pressure, the spiral will further coil. This effect can be monitored by visually tracking the movement of the indicator tip. Deformation that results is linearly related to the applied pressure difference and can be correlated to environmental pressure, or in this case, IOP.

Figure 5B:
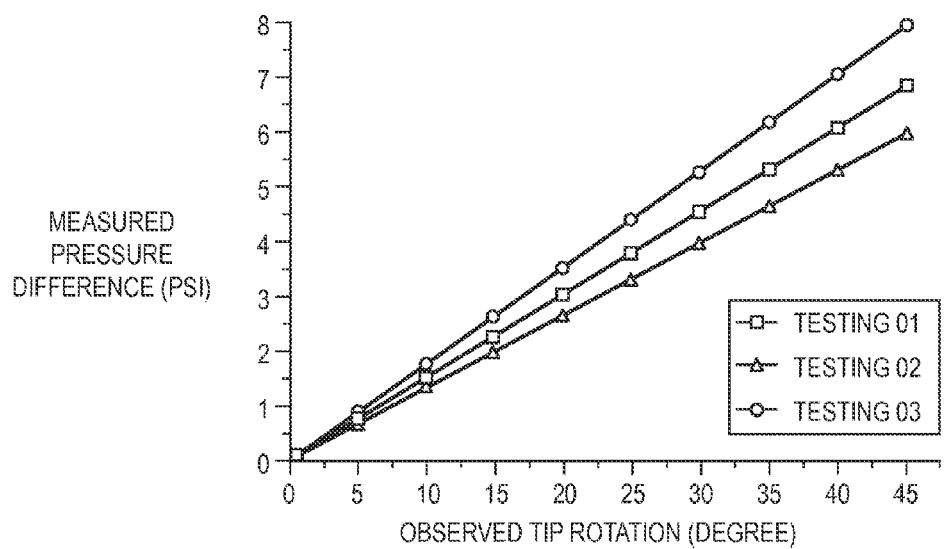
FIG. 5B plots observed rotation versus measured pressure difference, for the indicator tip of an IOP sensor in accordance with an embodiment of the present invention.

Sensor operation has been verified in air, isopropyl alcohol (IPA), and water. Observed tip rotation is visually recorded with the aid of optical magnification as the environmental pressure is increased. The results for water are shown in FIG. 5B. Measured sensitivities are 0.22°/mmHg (±9% variation in rotation angles) in IPA and 0.13°/mmHg in water (±15% variation). Sensitivity of the pressure sensor can be tuned by changing the number of coil turns. Increased sensitivity can be achieved by increasing the number of coil turns, decreasing the thickness of the tube walls, and increasing the aspect-ratio profile of the tube.

Implantable devices require mechanical attachment to the biological environment. This is conventionally achieved by sutures, tacking, or stapling, at the expense of increasing overall implant size through the addition of anchoring sites. Given the spatial constraints in the eye, and in order to minimize damage, it is desirable to implant and secure our sensor and GDD without needing sutures.

The logical choice for placement of the IOP sensor to facilitate optical readout would be behind the transparent cornea on the iris. In order to monitor movement of the indicator tip, the sensor should be securely attached to the iris. The surface topology of the iris consists of numerous folds resembling hills and valleys that can accommodate alternative mechanical attachment methods.

Figure 6A:
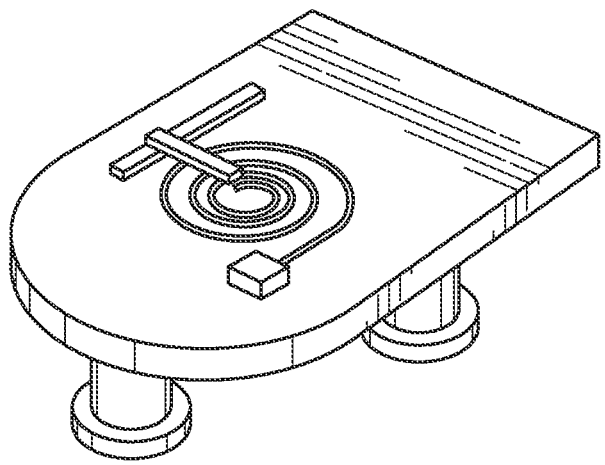
FIGS. 6A-B show top and bottom perspective views respectively, of an embodiment in accordance with the present invention of an IOP sensor on a silicon platform.
Figure 6B:
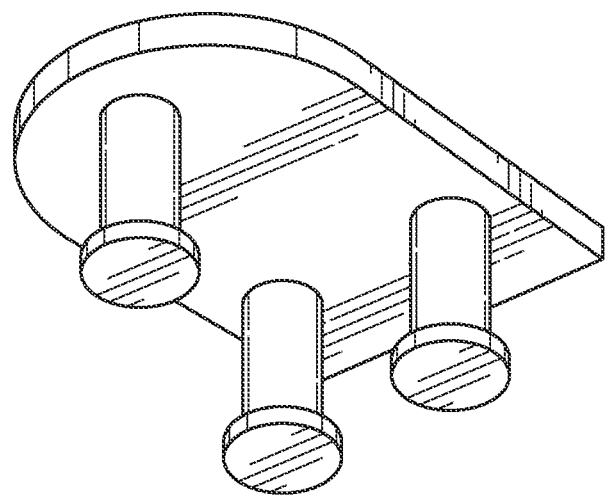

FIGS. 6A-B accordingly show simplified perspective views of a generic implant in accordance with an embodiment of the present invention. Tissue anchoring prototypes 600 comprising Velcro-like arrays 602 of parylene-covered silicon posts 604 were fabricated and implanted on the irises of rabbit eyes.

Fabrication of the posts can be integrated with the IOP sensor process. To enhance the adhesion of parylene, anchors are patterned and etched at future post sites according to Liger et al., "Robust Parylene-to-Silicon Mechanical Anchoring," in *MEMS* 2003. Kyoto, Japan, pp. 602-605 (2003), incorporated by reference herein for all purposes. Posts are then defined and etched using DRIE in a silicon substrate. Finally, the entire structure is coated with a biocompatible parylene layer.

The etched columnar anchors securely fastened the silicon plates to rabbit irises. The plates remained fastened even after vigorous shaking imposed on the eye by the surgeon. The force required to dislodge anchored structures will be determined. Currently, these structures are being integrated on the backside of an IOP sensor substrate, and will be used to hold the entire platform in place for visual inspection of IOP. Similar anchoring structures may also be applied to mechanically attach the GDDs.

Figure 6C:
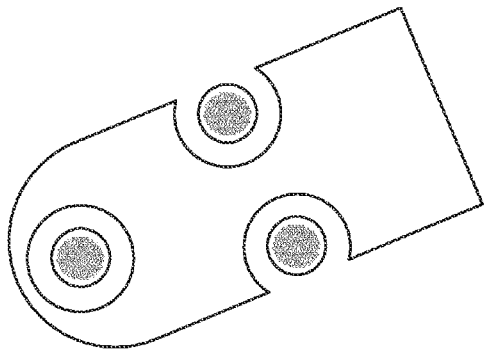
FIG. 6C is an electron micrograph from a bottom perspective of a silicon platform bearing an integrated tissue anchor of a first type.
Figure 6D:
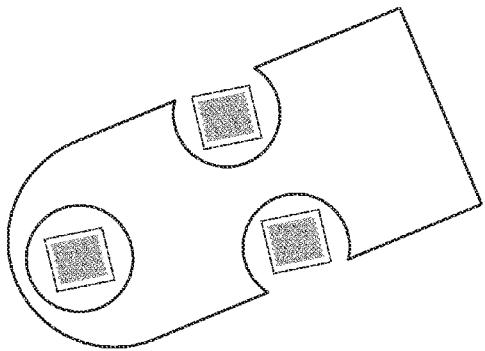
FIG. 6D is an electron micrograph from a bottom perspective of a silicon platform bearing an integrated tissue anchor of a second type.
Figure 6E:
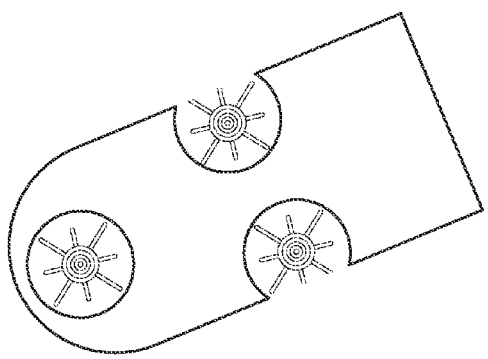
FIG. 6E is an electron micrograph from a bottom perspective of a silicon platform bearing an integrated tissue anchor of a third type.
Figure 6F:
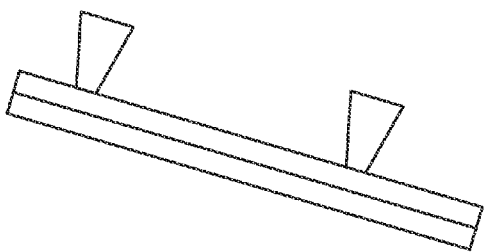
FIG. 6F is an electron micrograph from a side perspective of a silicon platform bearing an integrated tissue anchor.

FIGS. 6C-6F present electron micrographs of different layouts and views of various IOP sensors fabricated on a silicon platform (1.5 mm×0.75 mm) with integrated tissue anchors underneath. The circular anchor of FIG. 6C is 250 μm in diameter and 250 μm long. The square anchors of the embodiment of FIG. 6D measures 250 μm on a side. The radial arms of the embodiment of FIG. 6E are 8 μm in width. FIG. 6F shows a side view of one embodiment.

It is understood that the examples and embodiments described herein are for illustrative purposes only, and there can be other variations and alternatives. Various modifications or changes in light of the above description thereof will be suggested to persons skilled in the art and are to be included within the spirit and purview of this application and scope of the appended claims.

What is claimed is:

1. A method for relieving intra-ocular pressure comprising:
providing a drainage device comprising a hollow tube comprising parylene and having an open end for implantation into an eye and a closed end in a portion positioned to lie outside sclera of the eye;
implanting the open end of the hollow tube into the eye;
anchoring the hollow tube;
flowing fluid into the tube through the open end based upon a difference in ambient pressure and pressure within the eye; and
creating an opening in a portion of the hollow tube outside of the eye by applying a laser to a thinned portion along a length of the tube to allow the fluid to flow out of the tube.

2. The method of claim 1, wherein anchoring the tube comprises securing the tube in the eye by barbs extending from the tube.

3. The method of claim 1, further comprising monitoring an intra-ocular pressure (TOP) within the eye, wherein the opening is created when the monitored IOP exceeds a threshold.

4. The method of claims 1, wherein the drainage device further comprises a foldable arm.

5. The method of claim 1, wherein the foldable arm is located outside the eye.

6. The method of claim 1 wherein the fluid flows out of a second open end of the tube through a one-way valve configured to open where the pressure difference exceeds a threshold.

* * * * *

UNITED STATES PATENT AND TRADEMARK OFFICE
CERTIFICATE OF CORRECTION

| | | |
|---|---|---|
| PATENT NO. | : 8,585,630 B2 | Page 1 of 1 |
| APPLICATION NO. | : 13/555329 | |
| DATED | : November 19, 2013 | |
| INVENTOR(S) | : Ellis Fan-chuin Meng et al. | |

It is certified that error appears in the above-identified patent and that said Letters Patent is hereby corrected as shown below:

In the Claims

At column 13, claim 3, line 20, delete "(TOP)" and replace with --(IOP)--.

Signed and Sealed this
Twenty-fifth Day of March, 2014

Michelle K. Lee
*Deputy Director of the United States Patent and Trademark Office*